(12) United States Patent
Jons

(10) Patent No.: US 8,991,235 B2
(45) Date of Patent: Mar. 31, 2015

(54) METHOD OF TESTING MEMBRANES AND MEMBRANE-BASED SYSTEMS

(75) Inventor: Steven D. Jons, Eden Prairie, MN (US)

(73) Assignee: Dow Global Technologies LLC, Midland, MI (US)

( * ) Notice: Subject to any disclaimer, the term of this patent is extended or adjusted under 35 U.S.C. 154(b) by 1480 days.

(21) Appl. No.: 12/436,819

(22) Filed: May 7, 2009

(65) Prior Publication Data

US 2010/0281960 A1    Nov. 11, 2010

(51) Int. Cl.
*G01N 15/08* (2006.01)
*B01D 65/10* (2006.01)
*G01N 15/02* (2006.01)

(52) U.S. Cl.
CPC .......... *B01D 65/102* (2013.01); *G01N 15/0272* (2013.01)
USPC .............................................................. 73/38

(58) Field of Classification Search
USPC .............................................................. 73/38
See application file for complete search history.

(56) References Cited

U.S. PATENT DOCUMENTS

| | | | |
|---|---|---|---|
| 5,480,554 A | 1/1996 | Degen et al. | |
| 5,674,404 A | 10/1997 | Kenley et al. | |
| 5,905,197 A * | 5/1999 | Wilf | 73/86 |
| 6,370,943 B1 | 4/2002 | Glucina et al. | |
| 6,451,201 B1 | 9/2002 | Cadera et al. | |
| 6,838,002 B2 | 1/2005 | Zeiher et al. | |
| 7,011,758 B2 | 3/2006 | Rajagopalan et al. | |
| 7,012,678 B2 | 3/2006 | Enomoto et al. | |
| 7,216,529 B2 | 5/2007 | Ventresque et al. | |
| 2005/0050943 A1 | 3/2005 | Barber et al. | |
| 2007/0131556 A1 | 6/2007 | Lambie et al. | |
| 2008/0105038 A1* | 5/2008 | Jons et al. | 73/38 |
| 2008/0202242 A1 | 8/2008 | Mickols et al. | |

FOREIGN PATENT DOCUMENTS

| | | |
|---|---|---|
| EP | 1920821 | 10/2006 |
| EP | 2006016 | 12/2008 |
| EP | 2088127 | 8/2009 |
| JP | 06-320157 | 11/1994 |
| JP | 8-252440 | 10/1996 |
| WO | 0139870 | 6/2001 |
| WO | WO 2006/026011 | 3/2006 |

OTHER PUBLICATIONS

"Membrane Element Autopsy Manual," Water Treatment Technology Program Report #17, U.S. Bureau of Reclamation, 1996.
J. Lozier, et. al., "Microbial Removal and Integrity Monitoring of High-Pressure Membranes", AWWA Research Foundation, 2003.

(Continued)

*Primary Examiner* — Hezron E Williams
*Assistant Examiner* — Rodney T Frank
(74) *Attorney, Agent, or Firm* — Edward W. Black

(57) ABSTRACT

The invention includes methods for testing membranes and membrane-based systems by introducing particles into a feed liquid passing across the surface of a membrane wherein the particles have a size larger than the nominal cut-off of the membrane, and measuring the presence of the particles within a permeate solution which passes through the membrane. In one embodiment, the particles are selected from those which dissolve within the permeate solution after being measured. In another embodiment, the particles are selected from inorganic salts. Many additional embodiments are disclosed.

9 Claims, 1 Drawing Sheet

(56) References Cited

OTHER PUBLICATIONS

M.M. Nederlof, et. al., "Integrity of membrane elements, vessels and systems," Desalting and Water Purification Research Report 55, Bureau of Reclamation.

S. Adham, et. al., Monitoring the integrity of reverse osmosis membranes' Desalination 119, (1998), 142-150.

ASTM D6908-03, "Standard Practice for Integrity Testing of Water Filtration Membrane Sytems", ASTM International, West Conshohocken, PA (Jun. 2003), 1-13).

Laine, J.M. et al., "Acoustic sensor: a novel technique for low pressure membrane integrity monitoring," Desalination 119 (1998), 73-77.

"FilmTec Membranes: Probing Reverse Osmosis Systems," DOW Form No. 609-00235-0404, Dow Chemical, Midland, MI, (Nov. 1997).

D. Van Gauwbergen, et al., Macroscopic Fluid Flow Conditions in Spiral-Wound Membrane Elements, Desalination 110, (1997), 287-299.

Roth, et al., Sodium Chloride Stimulus-Response Experiments in Spiral Wound Reverse Osmosis Membranes: A New Method to Detect Fouling, Desalination 121, (1999), 183-193.

"Methods for Monitoring the Integrity of Reverse Osmosis Ans Nanofiltration Membrane Systems", Desalting and Water Purification Research Report No. 55, U.S. Bureau of Reclamation, 2000.

Ould-Dris, A., et al., "Analysis of cake build-up and removal in cross-flow microfiltration of $CaCO_3$ suspensions under varying conditions", Journal of Membrane Science 175 (2000) 267-283.

Mitsoyannis, A., et al., "Precipitation of Calcium Carbonate on Reverse Osmosis Membrane", Desalination, 21 (1977) 235-240.

Fradin, Benoit, et al., "Crossflow microfiltration of magnesium hydroxide suspensions: determination of critical fluxes, measurement and modeling of fouling", Separation and Purification Technology 16 (1999) 25-45.

\* cited by examiner

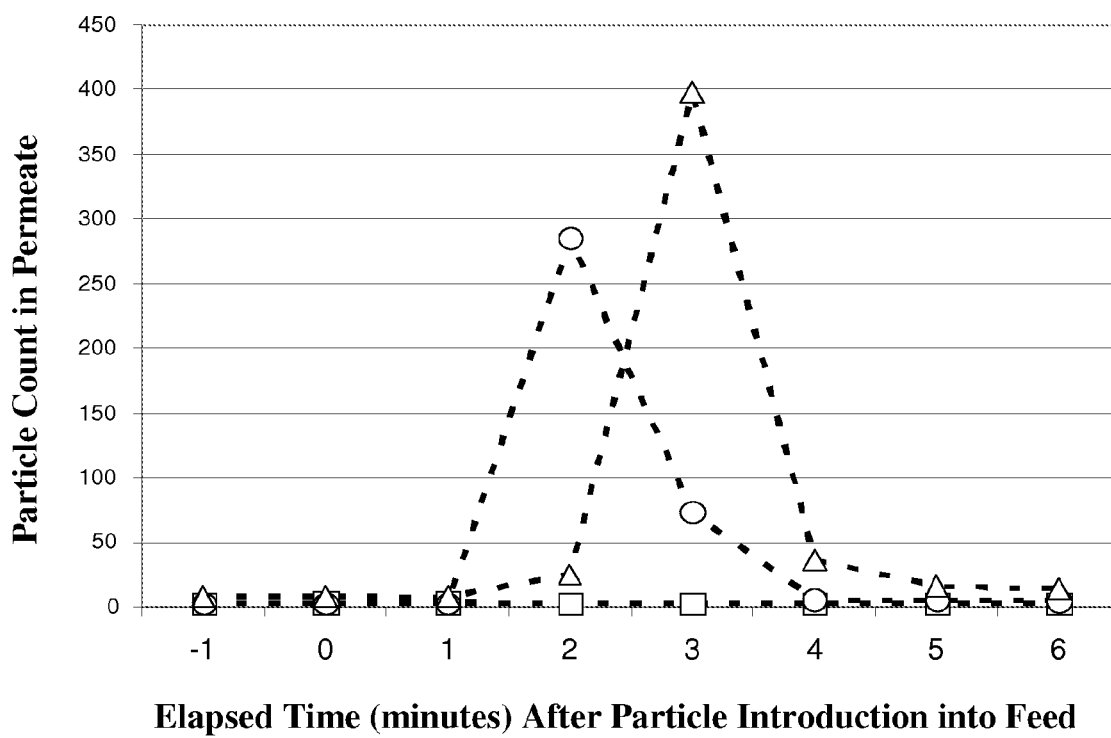

US 8,991,235 B2

METHOD OF TESTING MEMBRANES AND MEMBRANE-BASED SYSTEMS

TECHNICAL FIELD

The invention relates to methods for testing the integrity of membranes by introducing particles into an upstream feed liquid and measuring the presence of particles within the permeate.

BACKGROUND ART

Leaks often occur in membrane-based systems due to a variety of defects such as: pinholes, scratches or other defects in membranes; failed glue lines, seals and potting within membrane module construction; and misaligned seals or inter-connectors between modules within a membrane-based system. One known technique for testing systems for such leaks involves the introduction of particles into the feed liquid upstream from the membrane. The particles used in such testing typically have a size larger than the nominal cut-off of the membrane such that the detection of particles within the permeate can be correlated to a leak or defect within the system. Examples of particles used in such testing include: fluorescent microspheres as described in US 2008/0105038, latex particles as described in U.S. Pat. No. 5,480,554 and magnetic particles such as ferrites and transition metal oxides, sulfides, silicides and carbides as described in U.S. Pat. No. 7,011,758.

One aspect of such testing techniques is that the concentration of particles introduced within the feed liquid is much greater than that measured within the permeate solution, (e.g. often 1000 or event 100,000 times greater). At such high concentrations, many particles are cost prohibitive. Moreover, when used in high concentrations many particles foul the membrane, catalyze scale formation, and in some instances, catalyze the oxidation of the membrane. Depending upon the particle type and application, particles may also need to be recovered from the permeate and/or reject solution.

STATEMENT OF INVENTION

The invention includes methods for testing membrane-based systems by introducing particles into a feed liquid passing across a membrane. The presence of particles within the permeate can be measured and correlated to defects. In one embodiment, particles are selected from those which dissolve within the permeate after being measured. In another embodiment, particles are selected from inorganic salts. Many additional embodiments are disclosed.

BRIEF DESCRIPTION OF THE FIGURE

FIG. 1 is a graph showing the number of particles (4 to 5 µm) within the permeate solution of a spiral wound module, measured as a function of time after introduction into the feed liquid.

DETAILED DESCRIPTION

The invention includes a method for testing the integrity of membranes and membrane-based systems. For purposes of this description, the term "membrane-based system" includes an individual membrane, a membrane module and a system including one or more such modules. By way of example, the invention may be used to test: a flat sheet membrane such as a thin-film composite membrane, an individual spiral wound module including such a thin-film composite membrane and/or a system including one or more spiral wound modules arranged within a pressure vessel including various seals, interconnectors and fluid ports. Other examples include hollow fiber membranes, hollow fiber modules and systems including different types of modules, e.g. a system comprising a hollow fiber module as a pre-filter followed by a spiral wound element. As leaks may be attributed to a variety of defects within a system (e.g. torn membrane, failed glue lines, faulty potting, misaligned seals, etc.), it is often advantageous to test the entire membrane-based system in addition to or as an alternative to testing individual membranes or modules prior to incorporation within a system.

During standard operation of a membrane-based system, feed liquid passes across the surface of the membrane, and as a consequence of transmembrane pressure (typically generated by pressurizing the feed liquid or drawing a vacuum on the permeate side of the membrane), a portion of the feed liquid passes through the membrane to form a permeate solution. The portion of feed liquid not passing through the membrane is commonly referred to as a concentrate or "reject" solution. For purposes of the present description, use of the phrase "passing across" the membrane is intended to generically describe systems operating in a wide variety of flow configurations including: cross-flow, dead-end flow and variations thereof wherein varying portions of the reject solution are bled from the system.

The retention characteristics of a membrane are commonly described in terms of a "nominal cut-off". For microfiltration (MF) and ultrafiltration (UF) membranes, the nominal cut-off is often described in terms of a nominal particle size; whereas for nanofiltration (NF) and reverse osmosis (RO) membranes, the nominal cut-off is often described in terms of a nominal molecular weight. For purposes of the present description, the term "nominal cut-off" describes the size of species (solute) which is at least 90%, preferably at least 97% and more preferably at least 99% rejected by a defect-free membrane. The term "defect-free membrane" describes a membrane that is intact and without defects which would materially effect performance.

The present method includes the step of introducing particles into a feed liquid passing across a membrane and subsequently measuring (e.g. detecting) the presence of particles within the permeate solution. In one preferred embodiment, the particles are transient or ephemeral in that they remain present in the permeate solution long enough to be measured but then dissolve. The rate of dissolution should be slow enough to permit measurement within the permeate solution (e.g. at least 1 minute but preferably at least 5 minutes, and more preferably at least 10 minutes) but not so long as to persist. The rate of dissolution of a given particle may be dependant upon a variety of factors including the concentration and size (surface area) of the particle and the composition, temperature and pH of the solvent (e.g. permeate solution). For purposes of most systems, the concentration of particles in the permeate solution is sufficiently low (e.g. 0.00001 to 0.001 gram of particles per liter) not to be a significant factor in the rate of dissolution. Moreover, most systems operate within a temperature range of from about 5 to 65° C., thus temperature is also not typically a significant factor. While most membrane-based systems operate within a relatively narrow pH range, (e.g. from about 5 to 9), variations in pH can have a significant impact on the rate of dissolution of some particles. For example, particles of calcium carbonate and magnesium hydroxide are relatively stable (i.e. slow dissolution rates) at a pH of 9, but rapidly dissolve at a pH of 5. In distinction, such pH values have little effect on the rate of dissolution of most mono and disaccharides. For purposes of the present description, the term "dissolve" means that a given particle (e.g. of median size based upon the distribution of particles introduced into the feed liquid) decreases in size by at least 50% within 24 hours, preferably within 10 hours, and more preferably within 2 hours.

In the absence of a catastrophic defect, the concentration of particles in the feed and rejection solution is significantly higher than that of the permeate solution, e.g. from 0.001 to 10 g, but more preferably from 0.01 to 1 g of particles per liter of feed or rejection solution. Even when present at such higher relative concentrations, the particles preferably dissolve in the feed liquid and/or reject solution within 24 hours.

The use of such transient particles avoids a permanent deposition or entrainment of particles within the membrane or module (e.g. on the surface membrane or retained in a feed spacer). Further, it can avoid the need for recovery or removal from permeate or reject solutions, although re-use of reject solutions may be economically desirable in some cases. Many species of particles can be more quickly dissolved from most systems by exposure to mildly acidic solutions, e.g. aqueous solutions having a pH less than about 5.5, 5, or in some embodiments, less than 4.

In another embodiment, particles are selected from inorganic salts, including combinations of different species. Examples of applicable inorganic salts include salts of alkali and alkaline earth metals, (i.e. salts formed from Group I and Group II elements of the current IUPAC Period Table). Preferred metals include those from Group II, including magnesium, calcium and barium. Representative examples include calcium carbonate (e.g. calcite and aragonite) and magnesium hydroxide. Calcium carbonate in natural form (e.g. limestone, dolomite, marble, chalk and shells) and precipitated (e.g. via carbonization of calcium hydroxide) may be used. Non-limiting examples of commercially available calcium carbonate particles include food grade products from: Minerals Technologies such as CalEssence™ 450 PCC (4.5 μm) and Omya Corporation such as OMYA-CAL FG-4 AZ (3.5 μm). Examples of magnesium hydroxide particles include FloMag™ HUS (3.0 μm) available from Martin Marietta Magnesia Specialties LLC.

In a preferred embodiment, the inorganic salts are selected from those having a first ionization "$K_{sp}$" value at 25° C. of less than $1\times10^{-4}$ mol$^2$/L$^2$, or less than $1\times10^{-7}$ mol$^2$/L$^2$ or even less than $1\times10^{-9}$ mol$^2$/L$^2$. In other embodiments, the inorganic salt is selected from those having a first ionization $K_{sp}$ value at 25° C. of from about $1\times10^{-4}$ mol$^2$/L$^2$ to about $1\times10^{-13}$ mol$^2$/L$^2$, but preferably from about $1\times10^{-8}$ mol$^2$/L$^2$ to about $1\times10^{-13}$ mol$^2$/L$^2$. The symbol "$K_{sp}$" refers to the solubility product constant and is calculated from the free energies of formation of the substances as solids and those of the aqueous ions according to the formula: $\ln K_{sp} = -\Delta G°/RT$. $K_{sp}$ values are widely reported in the literature including the CRC Handbook of Chemistry and Physics.

In several embodiments, the particles are preferably non-magnetic, non-ferrite, non-silicide, non-silicate, non-carbide and/or non-sulfide.

The particles preferably have a size larger (e.g. 10×) than the nominal cut-off of the membrane being tested. Methods for calculating median particle sizes are well known in the art and are described in the literature, e.g. see Perry's Chemical Engineers Handbook. The term "particle size" or "size" with reference to particles refers to the mass-weighted median diameter of the particles. In most applications, particles are selected within a size range from about 0.1 to 100 μm (microns); however in many applications particles having sizes of from about 0.1 to 20 μm, or from about 0.1 to 10 μm, or from about 0.5 to 10 μm and in some embodiments from about 1 to 5 μm are preferred. The selection of particle size may be based upon the nominal cut-off of the membrane or other factors. For example, particles greater than 10 μm may less readily pass through intricacies of a brine spacer within a spiral wound module. Whereas, particles less than 0.1 μm, or even 0.5 μm, may more readily dissolve and thus be more sensitive the environmental variability. Another potential criterion for particle size selection may be the size of the solute or contaminate of most concern. For example, in applications where leakage of bacteria (e.g. Cryptosporidium) into the permeate is of primary concern, particles having a size of from about 0.5 to 5, or from about 1 to 5 μm may be selected.

The distribution of particle size is not particularly limited; however, in several embodiments a relatively narrow distribution is preferred. Use of narrow particle size distributions allows for the detection of the number of particles within a specific size range (i.e. at or near the median particle size), while excluding particles having sizes outside the desired range. This approach reduces the contribution from background particles and other artifacts (e.g. air bubbles) which are not related to defects or leaks. For example, in selected embodiments at least 70% (mass percent) and more preferably at least 90% of the particles have a diameter from about 0.5 to about 1.5 times the mass-weighted median particle diameter. The distribution of particle size may be narrowed by a variety of known techniques such as use of: screening, centrifuge, hydraulic cyclones, gravitational sedimentation, or by wet-grinding followed by aging as described in U.S. Pat. No. 6,592,837. The distribution of particle sizes may also be narrowed by introducing the particles into the feed liquid after being subject to at least one size-narrowing filtration operation. For example, the filtration operation may involve the step of filtering a solution of particles with a microfiltration or ultrafiltration membrane having an appropriate nominal cut off so that the resulting permeate solution excludes undesired particles which are larger than the nominal cut off. Additionally, or alternatively, the size-narrowing filtration operation may concentrate particles larger than a specific size (in the rejection solution) while passing undesired particles which are smaller than the nominal cut off. In this case, use of the reject solution avoids particles having a size smaller than desired. Such filtration operations limit the introduction of particles to those of most interest and further reduce the potential for blocking defects which then may go undetected. In one embodiment, at least one size narrowing filtration operation immediately precedes the introduction of particles to the feed liquid as part of the subject method. As such filtration operations may be performed under conditions which are particularly vulnerable to fouling (e.g. high concentrations of particles, operation under high recovery, use of particle sizes near the membrane's nominal cut-off), the use of transient particles may be particularly advantageous.

The manner of introducing particles into the feed liquid is not particularly limited. For example, a supply of feed liquid and particles may be pre-mixed and then used to test a membrane-based system. Alternatively, particles may be added to an existing feed liquid during operation of the system. The introduction of particles into the feed can be conducted under steady-state conditions wherein a feed liquid having a constant concentration of particles is passed across the membrane (e.g. for 30 minutes). Alternatively, the feed liquid containing the particles may be introduced as a short pulse which is passed across the membrane for a time period of a few seconds to a few minutes (e.g. 5 seconds to 10 minutes) as described in US 2008/0105038. Introduction of particles by way of a short pulse has several advantages (e.g. improved signal to noise ratio) and may be easily adapted to a system in operation. That is, particles may be "spiked" into the feed liquid over a short duration without taking the system off-line (e.g. depressurizing). The concentration of particles within the feed liquid is not particularly limited and will depend upon several factors including the size of the particles and the sensitivity of particle detectors. Most detectors provide a standard background signal with an average value and standard deviation. Thus, it may be preferable to introduce particles into the feed liquid at a concentration at least 1000 times, 10,000 times, or even at least 100,000 times the concentration corresponding to a response equal to the standard deviation of the background signal for the detector. In many applications, the concentration of particles in the feed liquid during testing is from about 0.001 to 10 g/L, but preferably from about 0.01 to 1 g/L. If the concentration of particles is too high, the particles may temporarily foul the membrane or block holes which then go "undetected".

The feed liquids for most applications are aqueous-based, such as those associated with industrial, agricultural or manufacturing processes, municipal water sources and ground and surface waters (e.g. lakes, streams, rivers, run-off, aquifers, etc.).

Measurement of particles within the permeate solution may be qualitative, quantitative or both. Simple detection of particles within the permeate solution may be sufficient for many applications, particularly when utilizing particles having relatively large dimensions which may be more easily detected. In many embodiments, particles within the permeate solution are measured as a function of time and the measurement can then be correlated with the introduction of particles into the feed liquid or detection of particles in the reject solution. As described in US 2008/0105038, such time dependant measurements can facilitate the identification of the type, magnitude and location of defects. When measured as a function of time, particles are preferably selected from those which are relatively stable in the permeate solution over the measurement time period, i.e. those which do not substantially dissolve within the measurement time period. Measurements are typically based upon a sample of permeate solution removed from the module or system. Particles within the permeate solution may be concentrated prior to measurement as described in US 2008/0105038. For example, the permeate solution may be fed through a defect-free "concentrating" module, such as a spiral wound module that substantially rejects (at least 90% rejection) the particles. The reject solution of the "concentrating module" thus becomes more highly concentrated in the particles. In order to mitigate fouling of the membrane within the concentrating module, the membrane may be washed, back-flushed or exposed to a mildly acidic or basic solution, e.g. an aqueous solution having a pH of less than about 5.5, 5 or 4. The use of selected transient or dissolvable particles is particularly advantaged in this high recovery system as any membrane fouling is only temporary.

Measurement of particles having specific size ranges may be made by a variety of known devices including particle counters which rely on conductivity (e.g. Beckman-Coulter's Multisizer™ 3 Coulter Counter), light blocking (e.g. Rosemount Analytical PC-1, and ChemTrac PC 2400 PS), light scattering (Lighthouse LPC), or in some applications by way of direct imaging (e.g. with the aid of light microscope, pulsed lasers and electronic cameras). Once measured, particle data may be evaluated. In some embodiments, the detection of any particles in the permeate solution may be indicative of a leak. In other embodiments, particle data may be compared with a reference in order to evaluate the integrity of the membrane-based system. The reference may include data from a variety of sources including data collected previously from the same system, data derived from experiments with or simulations of a similar system, or data retrieved from an established database.

In one embodiment, a membrane-based system comprising one or more membrane modules is tested by introducing particles within the feed liquid and measuring the presence of particles within the permeate solution produced by the system. By way of example, such a system may comprise a single spiral wound module within a pressure vessel as described in U.S. Pat. No. 6,299,772 or multiple spiral wound modules serially connected within a pressure vessel as described in US 2007/0272628—both of which are incorporated herein in their entirety. The system may also comprise modules arranged in parallel arrangement. In yet another embodiment, a membrane-based system may comprise different types of modules such as hollow fiber and spiral wound modules. For systems which include multiple modules, particle measurements may be based upon permeate samples for each module, or from the collective system.

In another embodiment the present method comprises: introducing particles into a feed liquid passing across the membrane wherein the particles have a size larger than the nominal cut-off of the membrane, and measuring the presence of particles within a permeate solution which passes through the membrane; wherein the particles dissolve within the permeate solution after being measured. The particles preferably dissolve within 24 hours, preferably within 10 hours and more preferably within 2 hours. In most embodiments, the permeate solution has a pH of from 5 to 9 and a temperature of from 5 to 65° C., and the particles are present in the permeate solution at concentrations below saturation, e.g. from 0.00001 to 1 grams per liter, but more commonly from 0.00001 to 0.01 grams per liter. In a preferred embodiment, the particles have a size from 0.1 to 10 µm. The step of measuring the presence of particles within the permeate solution preferably occurs within 10 minutes, more preferably within 2 minutes and in some embodiments within 1 minute after the introduction of particles within the feed liquid. As a consequence, the particles are preferably stable, i.e. do not dissolve, for at least 1 minute, preferably 5 minutes and in some embodiments at 10 minutes after introduction. For example, particles of sodium chloride dissolve too fast to meet these preferred criteria; whereas particles magnesium hydroxide and calcium carbonate are suitable.

In another embodiment, particles are selected from those which: a) do not dissolve within 1 minute when combined at a concentration of 0.01 g/L at 25° C. and 1 atm in a buffered aqueous solution (e.g. 0.1 M sodium phosphate aqueous solution) having a pH selected from of 5 and 9, but b) dissolve within 24 hours when combined at a concentration of 0.01 g/L at 25° C. and 1 atm in a buffered aqueous solution (e.g. 0.1 M sodium phosphate aqueous solution) having a pH selected from of 5 and 9. That is, the particles are stable enough to be measured during the testing period (typically at least 1 minute up to about an hour) but subsequently dissolve. For example, 4.5 µm particles of calcium carbonate will dissolve rapidly in an aqueous solution at a pH of 5; however the same particles are relatively stable in a solution at a pH of 9 so that they remain after 1 minute. In other embodiments, the particles dissolve at faster rates, e.g. particles decrease in size by at least 50% when combined in the above-described buffered solutions after 12 hours, 6 hours, 3 hours or even 1 hour. In another embodiment, particles are selected to satisfy the preceding criteria when introduced into the aforementioned buffered aqueous solutions at concentrations from 0.001 to 1 g/L. In still another embodiment, particles are selected to satisfy the preceding criteria and which have a particle size of from 0.1 to 10 µm. Examples of suitable particles include calcium carbonate and magnesium hydroxide.

In another embodiment, the particles are selected from those which: a) when combined in a buffered aqueous solution (e.g. 0.1 M sodium phosphate aqueous solution) at a concentration of 0.01 g/L at 25° C. and 1 atm at a pH of 5 or 9, the number of particles within 10% of the median size are reduced by a factor of more than two within 24 hours; and b) when combined in a buffered aqueous solution at a concentration of 0.01 g/L at 25° C. and 1 atm at a pH of 5 or 9, the number of particles within 10% of the median size are reduced by a factor of less than two within 1 minute.

In another embodiment, the pH of the feed liquid may be adjusted prior to or during introduction of particles so that particles are more stable during testing but rapidly dissolve thereafter. For example, for a membrane system which typically operates with a feed liquid having a pH of about 6, it may be desirable to introduce sufficient base to temporarily raise the pH of the feed liquid to about 9 prior to or during introduction of magnesium hydroxide particles. In this way, the particles are more stable during the testing period but rapidly dissolve following the test during continued operation of the system at the lower pH. In such embodiments, the pH of the feed liquid is modified by at least one pH unit, but more preferably two pH units during the introduction of the particles. More preferably, the pH adjustment is maintained for more than 30 seconds following the introduction of particles to allow particles to propagate through the permeate region.

In yet another embodiment, the membrane-based system comprises a UF or MF filtration followed by an RO filtration wherein feed liquid used in the RO filtration is the permeate solution of the prior UF or MF filtration system. In such an embodiment, the UF or MF filtration system may be part of a waste water treatment plant. The UF or MF filtration system may reject more than 99.99% of cryptosporidium oocysts and may be separately tested on a regular basis. The resulting permeate from the UF or MF filtration preferably has less than 0.001 oocyst/L. In one embodiment, the RO permeate solution can be used as drinking water.

EXAMPLES

A spiral wound element (model TW 30-1812-75) was obtained from FilmTec Corporation and tested in a series of successive test runs. The first set of test runs utilized a defect-free element (Test Element A). After the first set of test runs, a leak was induced near the permeate tube and re-tested under the same conditions (Test Element B). After the second set of test runs, the leak near the permeate tube was repaired, but a pin hole was created near the back of a membrane leaf. The element (Test Element C) was re-tested under the same conditions.

The testing conditions for each test run included operating the element at approximately 414 kPa using an aqueous feed liquid (conductivity of approximately 550 µmho) under the following conditions: 24° C., pH of 8 with a recovery of approximately 1000 ml/minute reject solution and 240 ml/minute of permeate solution. Particles of magnesium hydroxide (median particle size of 3 µm, obtained from Flo-Mag™ HUS obtained from Martin Marietta Magnesia Specialties LLC) were introduced into to the feed liquid during a 1 minute interval to form a pulse of feed liquid having an approximate particle concentration of 0.1 g/L. An additional test was conducted using a 10× concentration (approx. 1 g/L) of particles for Test Element A.

Particles present in the permeate solution of each test run were counted as a function of time (based upon the time of introduction of the particles into the feed liquid). The results of several runs are provided in Table 1 along with an additional series of testing on Test Element A using particles at a 10× concentration (approximately 1 g/L). FIG. 1 is a plot of averaged data from Table 1 wherein data for Test Element A is designated with squares (based upon testing with a feed solution having a 10× concentration of particles); data corresponding to Test Element B is designated with circles, and data corresponding to Test Element C is designated with triangles.

The conductivity of the permeate solutions of each element was measured during the introduction of particles. The permeate solution of Test Element A had a relatively low conductivity of approximately 7 µmho, whereas the conductivities of Test Element B and C were 20 and 50 µmho, respectively.

TABLE 1

|  | Time after introduction (min) | | | | | | | |
|---|---|---|---|---|---|---|---|---|
|  | −1 | 0 | 1 | 2 | 3 | 4 | 5 | 6 |
| Test Element A | 2 | 2 | 2 | 2 | 3 | 2 | 2 | 2 |
| Test Element A | 1 | 1 | 4 | 2 | 3 | 2 | 3 | 3 |
| Test Element A* | 2 | 3 | 3 | 2 | 2 | 1 | 2 | 2 |
| Test Element A* | 4 | 4 | 4 | 3 | 4 | 4 | 4 | 4 |
| Test Element B | 2 | 2 | 2 | 272 | 124 | 5 | 4 | 3 |
| Test Element B | 3 | 3 | 3 | 232 | 62 | 4 | 3 | 3 |
| Test Element B | 3 | 3 | 3 | 353 | 35 | 9 | 9 | 8 |
| Test Element C | 6 | 6 | 4 | 7 | 314 | 44 | 16 | 8 |
| Test Element C | 8 | 8 | 7 | 16 | 512 | 34 | 14 | 16 |
| Test Element C | 11 | 11 | 12 | 53 | 369 | 31 | 19 | 19 |

*tested using a 10X concentration of particles (i.e. approximately 1 g/L)

The invention is not particularly limited to a specific type, shape or construction of membrane, membrane module or membrane system; nor is the invention limited to a flow configuration. For example, the invention is applicable to flat sheet membranes and corresponding modules such spiral wound and plate & frame modules. The invention is also applicable to tubular and hollow fiber membranes along with corresponding modules incorporating the same. Applicable modules are used in a wide variety of applications including reverse osmosis (RO), nanofiltration (NF), ultrafiltration (UF) and microfiltration (MF) liquid separations which may operate in flow configurations such as cross-flow flow, dead-end flow or variations thereof. By way of illustrative example, the invention may be used in connection with spiral wound modules as described in US 2008/0105038, U.S. Pat. Nos. 6,881,336 and 5,681,467, each of which is incorporated herein in its entirety. Specific examples of commercially available spiral wound modules include: BW30-440i brackish water module, SW30-XLE-400i sea water desalination module and NF-400 nanofiltration module—all available from The Dow Chemical Company. Specific examples of applicable membranes for use in such spiral wound modules include those described in US 2008/0185332; US 2007/0251883; U.S. Pat. Nos. 6,723,241 and 6,280,853, each of which is incorporated herein in its entirety. By way of further example, the invention may also be used in connection with hollow fiber modules as described in US 2009/0026140. Specific examples of commercially available hollow fiber modules include models SFP-2660, SFP-2680 and SFP-2860 available from The Dow Chemical Company.

The invention is also applicable to membrane-based systems which comprise at least one membrane module interconnected with fluid ports (e.g. feed inlet(s), and permeate and reject stream outlets) as described in U.S. Pat. No. 6,299,772, or systems including multiple modules as described in US 2007/0272628, wherein individual modules may be interconnected by way interconnecting end caps as described in U.S. Pat. No. 6,632,356. In an alternative embodiment, a membrane system may comprise modules of different types such a system including an upstream UF hollow fiber module wherein permeate is directed to subsequent treatment with one or more downstream spiral wound NF or RO modules.

While principles of the invention are amenable to various modifications and alternatives forms, particular species have been described by way of examples and detailed description. It should be understood that the intent of this description is not to limit the invention to the particular embodiments described or examples provided, but rather to cover all modifications, equivalents, and alternatives falling within the spirit and scope of the disclosure. Many embodiments of the invention have been described and in some instances certain embodiments, selections, ranges, constituents, or other features have been characterized as being "preferred." Characterizations of "preferred" features should in no way be interpreted as designated such features as being required, essential or critical to the invention. It will be understood that certain features and sub-combinations are of utility and may be employed without reference to other features and sub-combinations. References to ranges of numerical values expressly include the end points of such ranges.

The invention claimed is:

1. A method for testing a membrane-based system comprising:
   a) introducing particles into a feed liquid passing across the membrane wherein the particles have a size larger than the nominal cut-off of the membrane and which dissolve within the feed solution within 24 hours, and
   b) measuring the presence of the particles within a permeate solution which passes through the membrane;
   wherein the method is characterized by selecting particles which dissolve within the permeate solution after being measured.

2. The method of claim 1 wherein the particles comprise an inorganic salt.

3. The method of claim 2 wherein the inorganic salt comprises at least one metal selected from alkali and alkaline earth metals.

4. The method of claim 3 wherein the inorganic salt has a first ionization $K_{sp}$ value at 25° C. of less than $1\times10^{-4}$ mol$^2$/L$^2$.

5. The method of claim 2 wherein the inorganic salt is selected from at least one of: calcium carbonate and magnesium hydroxide.

6. The method of claim 1 wherein the particles have mass-weighted median diameter of from about 0.1 to about 10 microns.

7. The method of claim 1 wherein the distribution of particle sizes is narrowed by introducing the particles into the feed liquid after being subject to at least one size-narrowing filtration operation.

8. The method of claim 1 wherein at least 90 mass percent of the particles have a diameter from about 0.5 to about 1.5 times the mass-weighted median particle diameter.

9. The method of claim 1 wherein particles are introduced into the feed liquid to form a concentration of from 0.001 to 10 g/L.

* * * * *